United States Patent
Allen et al.

(10) Patent No.: US 9,763,872 B2
(45) Date of Patent: *Sep. 19, 2017

(54) SHAKEABLE VOLUMIZING MASCARA

(71) Applicant: Coty Inc., New York, NY (US)

(72) Inventors: Nykol Allen, Plainfield, NJ (US); Glenn Allen, Lake Hiawatha, NJ (US); Dhaval Patel, Baskin Ridge, NJ (US); Rossana Lanza, Glen Rock, NJ (US)

(73) Assignee: Coty Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,824

(22) Filed: Feb. 4, 2016

(65) Prior Publication Data
US 2016/0228350 A1 Aug. 11, 2016

Related U.S. Application Data

(60) Provisional application No. 62/112,461, filed on Feb. 5, 2015.

(51) Int. Cl.
| | | |
|---|---|---|
| A61K 8/81 | (2006.01) |
| A61K 8/92 | (2006.01) |
| A61K 8/19 | (2006.01) |
| A61K 8/25 | (2006.01) |
| A61K 8/31 | (2006.01) |
| A61K 8/34 | (2006.01) |
| A61K 8/36 | (2006.01) |
| A61K 8/41 | (2006.01) |
| A61K 8/49 | (2006.01) |
| A61K 8/55 | (2006.01) |
| A61K 8/58 | (2006.01) |
| A61K 8/88 | (2006.01) |
| A61Q 1/10 | (2006.01) |
| A61K 8/04 | (2006.01) |

(52) U.S. Cl.
CPC .............. *A61K 8/927* (2013.01); *A61K 8/042* (2013.01); *A61K 8/19* (2013.01); *A61K 8/25* (2013.01); *A61K 8/31* (2013.01); *A61K 8/34* (2013.01); *A61K 8/345* (2013.01); *A61K 8/361* (2013.01); *A61K 8/41* (2013.01); *A61K 8/498* (2013.01); *A61K 8/4973* (2013.01); *A61K 8/55* (2013.01); *A61K 8/585* (2013.01); *A61K 8/8147* (2013.01); *A61K 8/88* (2013.01); *A61K 8/922* (2013.01); *A61Q 1/10* (2013.01); *A61K 2800/5922* (2013.01)

(58) Field of Classification Search
CPC .......... A61Q 1/10; A61Q 19/00; A61Q 19/04; A61Q 5/06; A61Q 5/12; A61Q 19/02; A61Q 19/08; A61Q 19/10; A61Q 5/02; A61Q 17/00; A61Q 1/02; A61Q 1/12; A61Q 7/00; A61Q 19/007; A61Q 5/10; A61Q 5/00; A61Q 17/005; A61Q 17/04; A61Q 19/001; A61Q 3/00; A61K 8/585; A61K 8/25; A61K 8/55; A61K 8/922; A61K 8/927; A61K 8/8147; A61K 8/88; A61K 8/0291; A61K 8/0295; A61K 8/34; A61K 8/361; A61K 8/37; A61K 8/44
See application file for complete search history.

(56) References Cited

U.S. PATENT DOCUMENTS

| | | |
|---|---|---|
| 5,800,825 A | 9/1998 | Mcmullen |
| 2008/0119570 A1 | 5/2008 | Brieva et al. |
| 2012/0003171 A1 | 1/2012 | Bui et al. |
| 2013/0164241 A1 | 6/2013 | Foley et al. |
| 2014/0186282 A1 | 7/2014 | Patel et al. |

FOREIGN PATENT DOCUMENTS

WO    WO-2016/126965 A1    8/2016

OTHER PUBLICATIONS

"International Application Serial No. PCT/US2016/016604, International Search Report mailed May 20, 2016", 3 pgs.
"International Application Serial No. PCT/US2016/016604, Written Opinion mailed May 20, 2016", 6 pgs.

*Primary Examiner* — Nannette Holloman
(74) *Attorney, Agent, or Firm* — Schwegman Lundberg & Woessner, P.A.

(57) ABSTRACT

Inventive embodiments disclosed here include a shakeable gel mascara. The shakeable gel mascara includes wax components that are about twenty percent less than wax components in other gel mascara formulations.

11 Claims, 7 Drawing Sheets

SHAKEABLE VOLUMIZING MASCARA

CLAIM OF PRIORITY

This patent application claims the benefit of priority of U.S. Provisional Patent Application Ser. No. 62/112,461 filed Feb. 5, 2015, which is hereby incorporated by reference herein in its entirety.

FIELD

Inventive embodiments disclosed herein relate to a shakeable volumizing mascara and to methods of the making shakeable volumizing mascara.

BACKGROUND

The ancient Egyptians believed that the eyes were windows to the soul and that it was important to conceal them from evil spirits with eye liner and mascara. The first mascara was made of ingredients that included kohl, crocodile dung, water and honey. This mascara was applied with bone and ivory applicators.

In 1913, Eugene Rimmel created the first mass produced non-toxic mascara, not to drive away evil spirits but impart length and volume to eyelashes. The Rimmel mascara was made from a mixture of petroleum and black coal dust.

SUMMARY

Figure 1B:
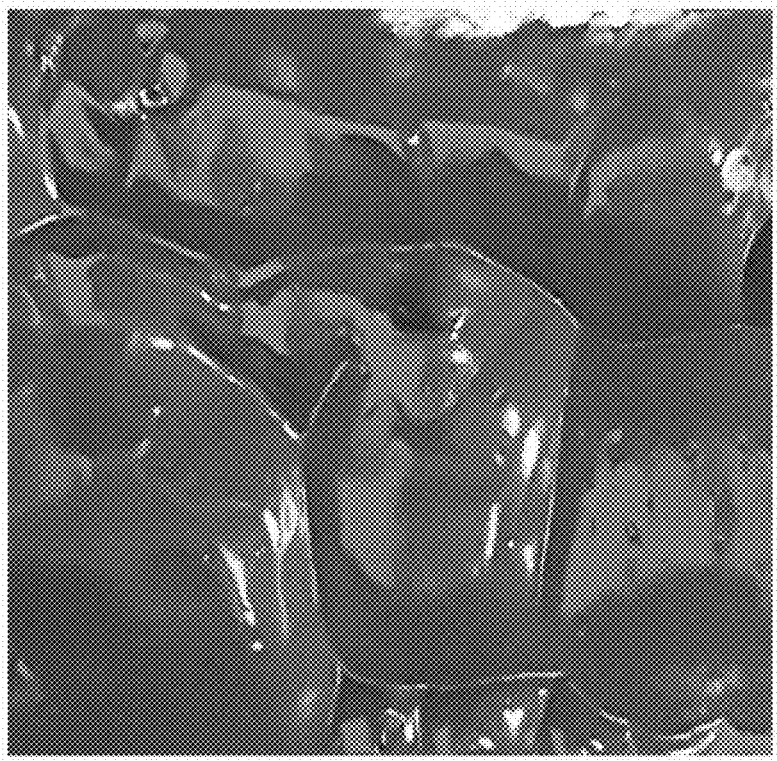
FIG. 1B illustrates a top plan view of a section of the shakable mascara of FIG. 1A.

Inventive embodiments disclosed herein include a shakeable gel mascara formulation. The formulation includes the following ingredients:

| Stage 1 | |
|---|---|
| Stearic Acid, Cosmetic Grade | 0.800 |
| Carnauba Wax Prime Yellow 2442 | 4.800 |
| Paracera P | 3.840 |
| Candelilla Wax 2039Y | 1.600 |
| 8104 Kahl White Beeswax | 5.600 |
| Stage 2 | |
| Deionized Water | 58.460 |
| Trilon BD | 0.100 |
| Stage 3 | |
| Laponite XLG | 1.500 |
| Stage 4 | |
| Tween 20 | 2.500 |
| Stage 5 | |
| Emulsiphos | 2.500 |
| Stage 6 | |
| Black Iron Oxide C33-5000 | 3.250 |
| Black Iron Oxide C33-6000 | 6.750 |
| Orgasol 4000EXD Nat Cos Caresse | 2.000 |
| Stage 7 | |
| DC 749 | 1.600 |
| Stage 8 | |
| Euxyl PE 9010 | 0.900 |
| Stage 9 | |
| Sodium Hydroxide, 10% Solution | 0.800 |
| Stage 10 | |
| WorleeMicromer C50/25 | 3.000 |

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Inventive embodiments disclosed herein relate to shakeable, thixotropic gel mascara formulation embodiments having a volumizing effect when applied to eyelashes. By "volumizing" is meant that eyelashes have an increased diameter and length due to the application of mascara. The shakeable mascara. formulation embodiments disclosed herein are sweat-proof, heat-proof and humidity-proof. The shakeable formulation embodiments include a combination of both soft and hard waxes along with a film-forming complex, which is a combination of cyclopentasiloxane and trimethylsiloxysilicate, and a combination of Polysorbate 20, water, as well as isopropyl alcohol and ammonium acrylates copolymer, and hydrogenated palm glycerides, potassium cetyl phosphate, as well as lithium magnesium sodium silicate, which is a natural clay, and iron oxides.

The shakeable mascara formulation embodiments disclosed herein are effective for instantly and visibly curling lashes, forming a curl on an eyelash having a duration of at least twenty-four hours. The curl is due, in particular, to the combination of both soft and hard waxes along with the film-forming complex.

The shakeable formulation embodiments disclosed herein display an instant lash volume increase due to the combination of both soft and hard waxes, along with a Nylon blend, Orgasol 4000EXD Nat Cos Caresse/Nylon-6/12, which contains both hydrophobic/hydrophilic properties that add instant volume to each lash.

The shakeable formulation embodiments are shaken with a container that, in one embodiment, is a plastic component containing a shakeable stainless steel cylinder that mixes the thixotropic mascara. For other embodiments, the container is glass. For other embodiments, the stainless steel cylinder is coated with a polymeric material. For other embodiments, a structure other than a cylinder, such as a sphere, is employed. The container is filled within a specific weight range, such that the shakeable weight constantly mixes the mascara such that it applies fresh longer and lasts longer.

With conventional mascara formulations, consumers complain that their mascara becomes gummy and dries out over time. This is due to much of their mascara getting caught on the wiper at the top of the container, where the wiper does not mix with the mascara at the base of the container. With the formulation embodiments of the present invention, the stainless steel weight mixes the mascara from around the wiper with the remaining mascara so that it is constantly freshened and is more volumizing so it lasts longer.

The shakeable mascara formula embodiments include a thixotropic gel such that the mascara's viscosity liquifies when agitated/shaken and stiffens quickly when agitation stops. The shakeable formula embodiments are buttressed with gum to provide body. The thixotropic gel is critical for this shakeable application.

The shakeable mascara formula embodiments have the usual combination of waxes used to make mascara to enhance beauty benefits such as curling, volumizing, separating, and lengthening the lashes, and include a film-forming agent to provide cohesion for an even application. The shakeable formula embodiments include a neutralizing agent, and any number of botanical extracts for cosmetic claims, such as collagen and keratin to aid in strengthening the eye lashes, for instance.

The shakeable mascara formulation embodiments are thixotropic gel systems that are typically shaken in a container having a stainless steel weight in the component.

One shakeable mascara formulation embodiment displays an increase in eyelash volumizing. The formulation is packaged in a container that promotes shaking and that includes a stainless steel weight. The shakeable mascara formulation embodiment is as follows:

| Formula 1 | |
|---|---|
| Ingredient | Percent (w/w) |
| Stage 1 | |
| Stearic Acid, Cosmetic Grade | 0.800 |
| Carnauba Wax Prime Yellow 2442 | 4.800 |
| Paracera P | 3.840 |
| Candelilla Wax 2039Y | 1.600 |
| 8104 Kahl White Beeswax | 5.600 |
| Stage 2 | |
| Deionized Water | 58.460 |
| Trilon BD | 0.100 |
| Stage 3 | |
| Laponite XLG | 1.500 |
| Stage 4 | |
| Tween 20 | 2.500 |
| Stage 5 | |
| Emulsiphos | 2.500 |
| Stage 6 | |
| Black Iron Oxide C33-5000 | 3.250 |
| Black Iron Oxide C33-6000 | 6.750 |
| Orgasol 4000EXD Nat Cos Caresse | 2.000 |
| Stage 7 | |
| DC 749 | 1.600 |
| Stage 8 | |
| Euxyl PE 9010 | 0.900 |
| Stage 9 | |
| Sodium Hydroxide, 10% Solution | 0.800 |
| Stage 10 | |
| WorleeMicromer C50/25 | 3.000 |

The shakeable mascara embodiment disclosed in Table 1 is distinguishable from other gel mascara formulations because it includes about 20% less wax, as shown in Table 2. Formula 1 is the shakeable mascara formula of the present invention. Formula 2 is a gel mascara that is not shakeable.

TABLE 2

| Ingredient | Formula 2 (% w/w) | Formula 1 (% w/w) |
|---|---|---|
| Denatured Alcohol | 0.2250 | |
| Ammonium Acrylates Copolymer | 1.1730 | 0.7350 |
| Beeswax | 7.0000 | 5.6000 |
| Carnauba Wax | 6.0000 | 4.8000 |
| Cyclopentasiloxane | 1.0000 | 0.8000 |
| Disodium Deceth-6 Sulfosuccinate | 0.1200 | |
| Disodium EDTA | 0.0900 | 0.0900 |
| Ethylhexylglycerin | 0.0900 | 0.0900 |
| Candelilla Wax | 2.0000 | 1.6000 |
| Hydrogenated Palm Glycerides | 1.2250 | 1.2250 |
| Iron Oxides | 10.0000 | 10.0000 |
| Laureth-30 | 0.0450 | |
| Lithium Magnesium Sodium Silicate | 1.5000 | 1.5000 |
| Nylon-6/12 | 2.0000 | 2.0000 |
| Paraffin | 4.8000 | 3.8400 |
| Phenoxyethanol | 0.8091 | 0.8091 |
| Polysorbate 20 | 2.4250 | 2.4250 |
| Potassium Cetyl Phosphate | 1.2750 | 1.2750 |
| Sodium Dehydroacetate | 0.0120 | |
| Sodium Hydroxide | 0.1000 | 0.0800 |
| Stearic Acid | 1.0000 | 0.8000 |

TABLE 2-continued

| Ingredient | Formula 2 (% w/w) | Formula 1 (% w/w) |
|---|---|---|
| Tocopherol | 0.0009 | 0.0009 |
| Trimethylsiloxysilicate | 1.0000 | 0.8000 |
| Water | 56.1100 | 61.5300 |

Formula 1 includes a combination of waxes to make a mascara to enhance beauty benefits such as curling, volumizing, separating, and lengthening the lashes and includes a film-forming agent to provide cohesion for an even application.

Trilon BD, manufactured by BASF, includes the disodium salt of ethylenediaminetetraacetic acid (EDTA) in a concentration of 90% w/w, and water in a concentration of 10% w/w.

Laponite XLG is a synthetic layered silicate with a low heavy metals content. It is insoluble in water but hydrates and swells to give clear and colorless colloidal dispersions in water or aqueous solutions of alcohol. At concentrations of 2% or greater in water, highly thixotropic gels are obtained. Once the gels are formed, waxes are added along with colorants into the gel suspension. It is possibly a double colloidal dispersion and the finished product is an emulsion. Laponite XLG is manufactured by BYK Additives Ltd. in Widnes, U.K.

Tween 20, also known as Polysorbate 20, is a polysorbate surfactant whose stability and relative non-toxicity allows it to be used as a detergent and emulsifier. Tween 20 has a chemical formula of $C_{58}H_{114}O_{26}$, a molar mass of 1227.54 g/mol and a density of 1.10 g/cm(3).

Emulsiphos is potassium cetyl phosphate (and) hydrogenated palm glycerides, manufactured by Symrise AG, located in Teterboro, N.J.

Black iron oxides C33-5000 and C33-6000 are both manufactured by Sun Chemical Corp. in Cincinnati, Ohio. Other black iron oxides are also suitable.

Orgasol 4000EXD Nat Cos Caresse is a copolyamide 6/12, also called Nylon-6/12. This material is manufactured by Arkema France.

Paracera P wax is a paraffin manufactured by Paramelt, located worldwide.

Euxyl PE 9010 is phenoxyethanol and ethylhexylglycerin. The material is manufactured by Schulke Inc. and typically acts as a preservative.

Dow Corning (DC) 749 Fluid is a blend of approximately 50 percent high molecular weight resin and 50 percent volatile, low viscosity cyclopentasiloxane.

WorleeMicromer C50/25 includes ammonium acrylates copolymer; water, CAS #7732-18-5; and isopropyl alcohol, CAS #67-63-0. WorleeMicromer C50/25 is manufactured by Worlee-Chemie GmbH of Hamburg, Germany.

Variation of water content in the formulation changes the degree of volumizing. A greater amount of water thins the formulation and reduces volumizing. In some formulation embodiments, one or more of the following ingredients are eliminated: Laponite (synthetic layered silicate), Orgasol 4000EXD Nat Cos Caresse (Nylon-6/12), DC749, Worlee-Micromer C50/25, sodium hydroxide, Emulsiphos, along with any of the waxes in Stage 1.

Another embodiment includes a mascara, comprising:
water in a concentration of at least about 45% by weight;
disodium EDTA;
Polysorbate 20;
black iron oxide;
one or more waxes selected from the group consisting of beeswax, carnauba wax, and paraffin in a concentration of 15-20% by weight; and
a synthetic layered silicate, insoluble in water, in a concentration effective for forming a colloidal dispersion with the water.

A method of making a gel volume mascara, comprising:
preparing a first phase of deionized water and disodium ethylenediaminetetraacetic acid (EDTA) by adding the disodium EDTA to the deionized water;
adding a surfactant to the first phase to make a second phase;
preparing a colloidal dispersion;
adding a particulate colorant to the colloidal dispersion to make a third phase and adding the third phase to the second phase to make a fourth phase; and
preparing a wax phase comprising one or more of stearic acid, carnauba wax, paraffin wax, candelilla wax or beeswax to make a wax phase and adding the wax phase to the third phase to make a fifth phase; and adding phenoxyethanol and ethylhexylglycerin to the fifth phase to make the gel volume mascara.

For some embodiments, the method further comprises adding a phase to the first phase of deionized water and disodium EDTA that comprises a synthetic layered silicate with low heavy metals content.

For some embodiments, the method further comprises potassium cetyl phosphate and hydrogenated palm glycerides, added to the second phase.

EXAMPLE 1

Figure 1A:
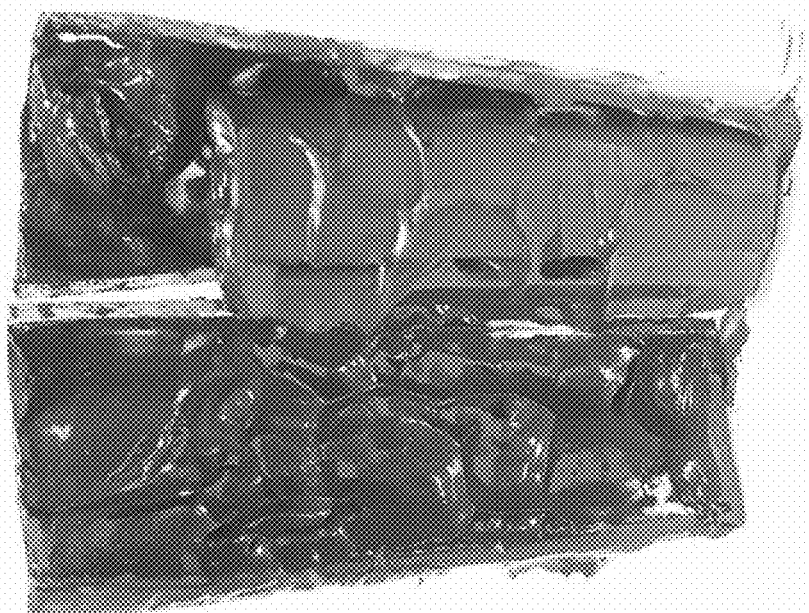
FIG. 1A illustrates a cross-sectional view of shakable mascara in a pack that had been opened but not used.
Figure 2B:
FIG. 2B illustrates a top plan view of a section of the shakable mascara of FIG. 2A.
Figure 2A:
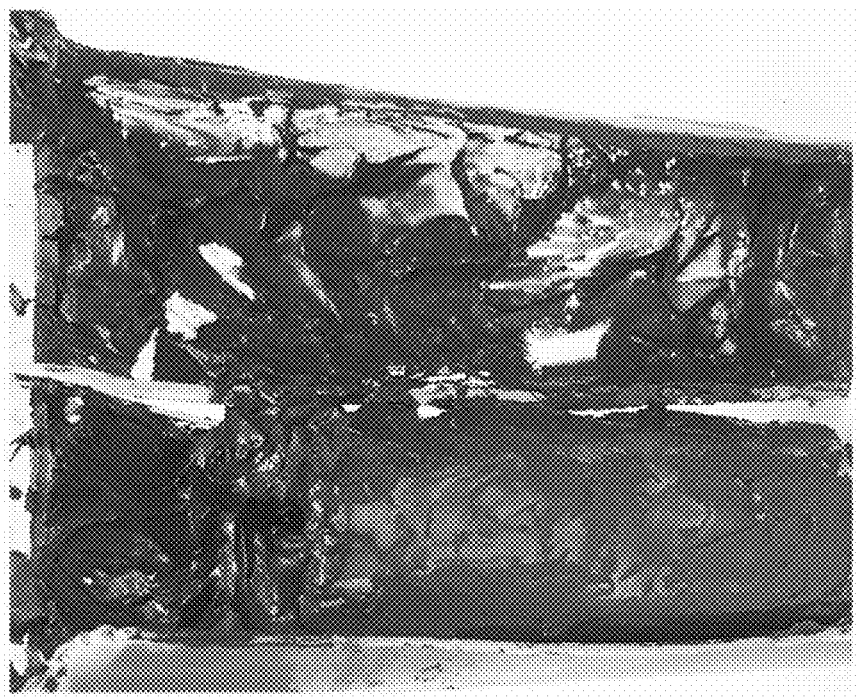
FIG. 2A illustrates a cross-sectional view of shakable mascara in a pack that had been opened and used for twelve weeks but was not shaken.
Figure 3B:
FIG. 3B illustrates a top plan view of a section of the shakable mascara of FIG. 3A.
Figure 3A:
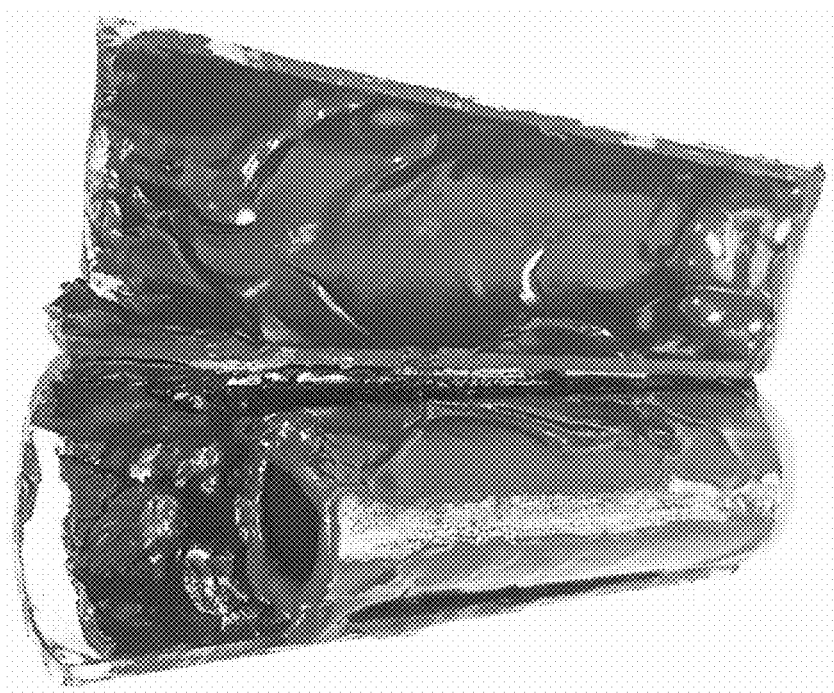
FIG. 3A illustrates a cross-sectional view of shakable mascara in a pack that had been opened and used for twelve weeks and was shaken.

The shakable mascara disclosed herein maintains its smoothness and is clump free when applied to hair for extended periods of time. FIGS. 1A and 1B illustrate the shakable mascara at the time that a package is opened. The mascara is smooth, without clumps. After twelve weeks of use, the shakable mascara of FIGS. 1A and 1B continues to show a smooth mascara, without clumps, as shown in FIGS. 2A and 2B. The mascara shown in FIGS. 2A and 2B was not shaken. FIGS. 3A and 3B show the mascara of FIGS. 2A and 2B, after the mascara was shaken. The intensity, that is, blackness and gloss of the shakable mascara, especially when shaken remains within specification over time and use compared to conventional mascara that appears dull and matte. The viscosity of the shakable mascara remains within specification over use compared to conventional mascara wherein viscosity increases significantly and out of specification.

Figure 4A:
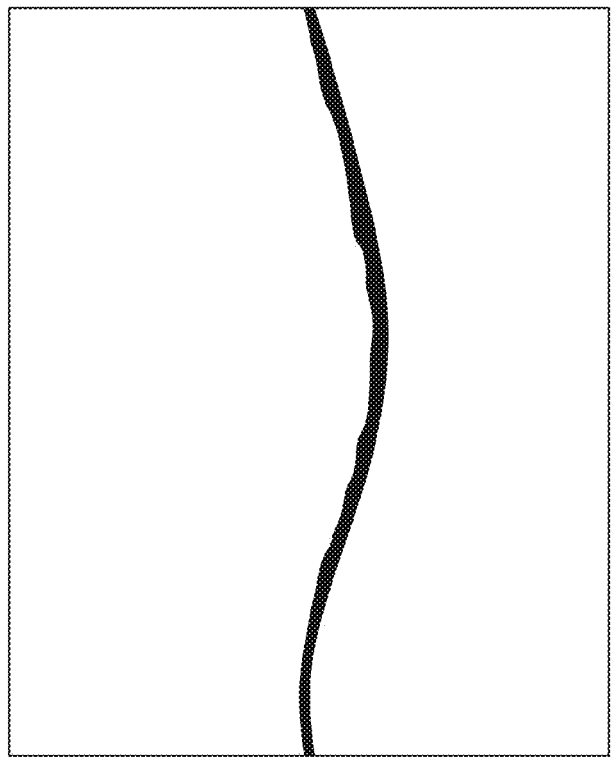
FIG. 4A illustrates a perspective view of a human strand of hair that had never been contacted with mascara.
Figure 4B:
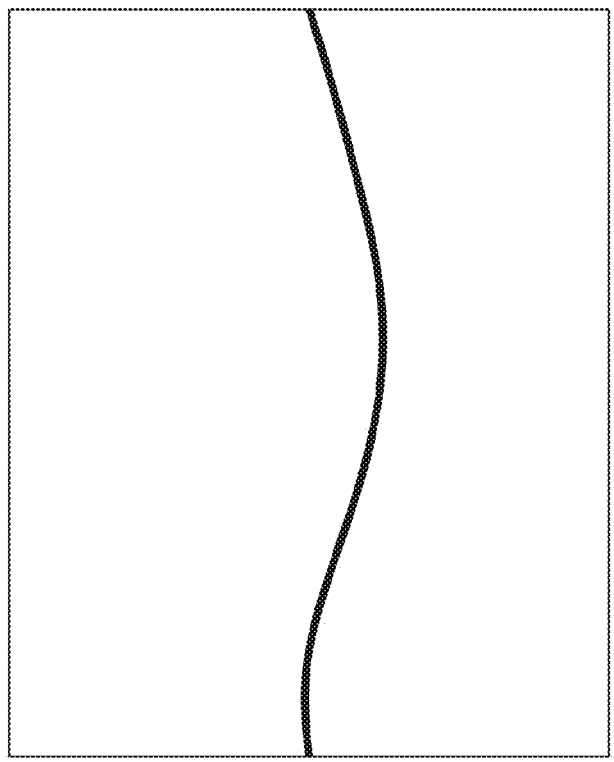
FIG. 4B illustrates a perspective view of the hair of FIG. 4A that had been contacted with a conventional, non-shakable mascara, for one time.

FIG. 4A illustrates a strand of hair that had never been contacted with mascara. FIG. 4B illustrates the hair of FIG. 4A, to which a conventional, non-shakable mascara had been applied. Mascara clumping and uneven distribution are observable.

Figure 5B:
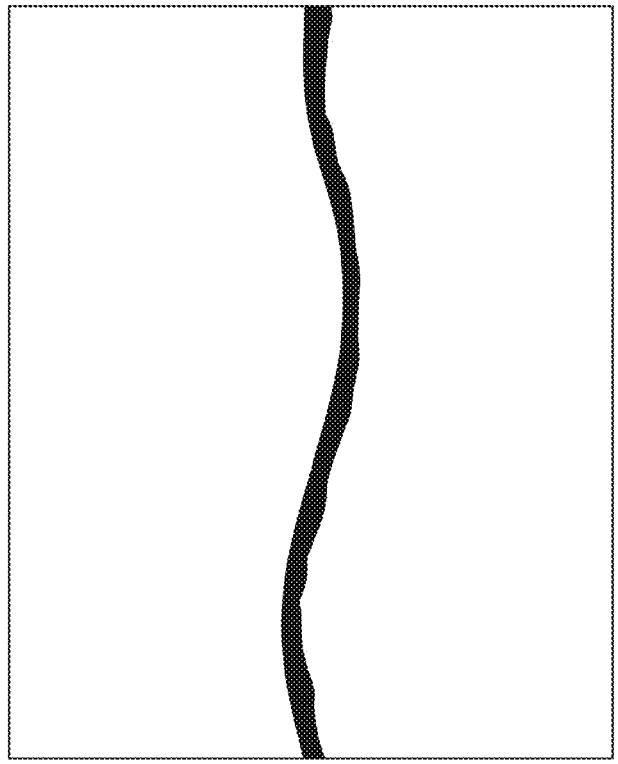
FIG. 5B illustrates a perspective view of the hair of FIG. 5A that had been contacted with a conventional, non-shakable mascara, for twelve weeks.
Figure 5A:
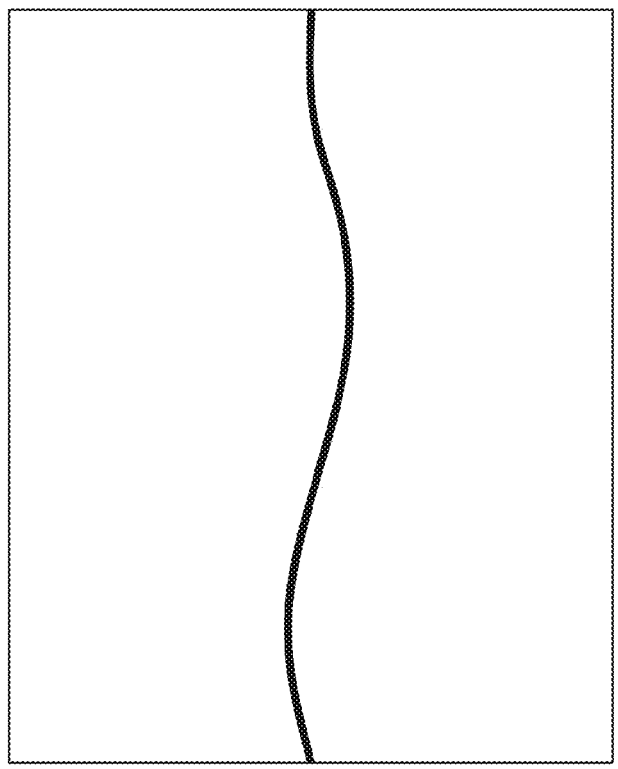
FIG. 5A illustrates a perspective view of a human strand of hair that had never been contacted with mascara.

FIG. 5A illustrates a strand of hair that had never been contacted with mascara. FIG. 5B illustrates the hair of FIG. 5A, to which a conventional non-shakable mascara had been applied over a period of twelve weeks. Mascara clumping and uneven distribution were observable.

Figure 6B:
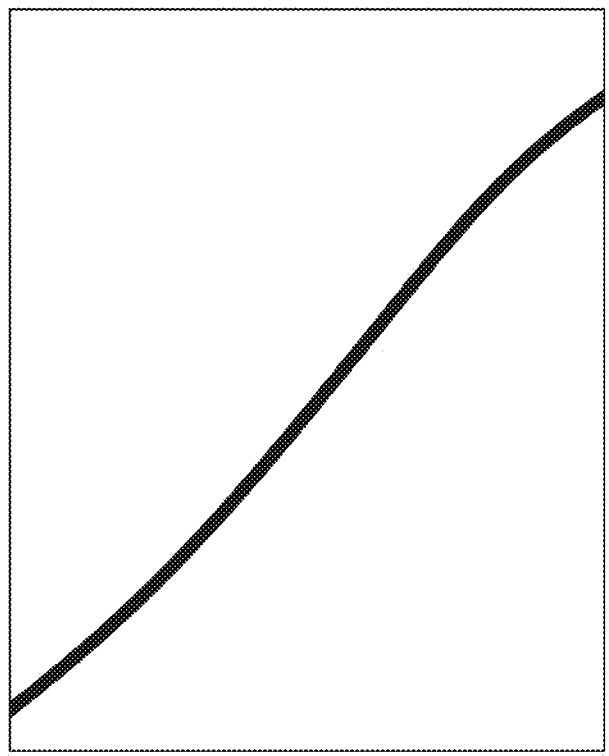
FIG. 6B illustrates a perspective view of the hair of FIG. 6A that had been contacted with a shakable mascara embodiment, for one time.
Figure 6A:
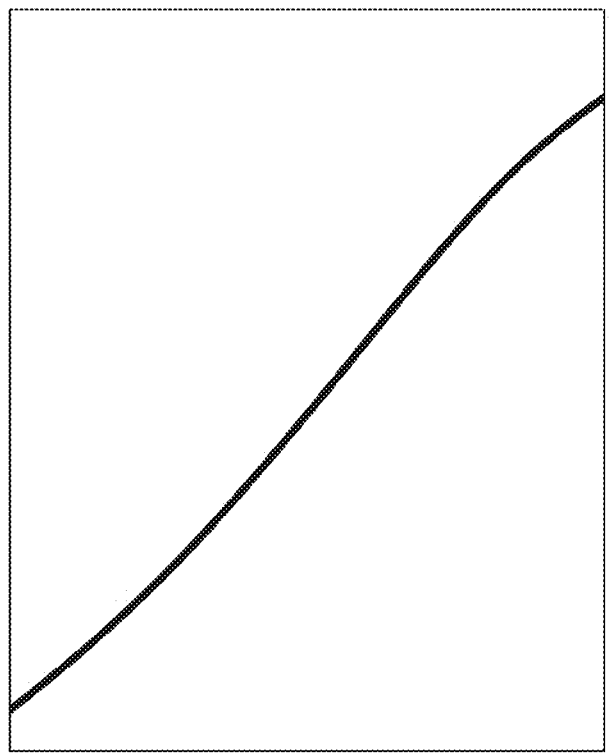
FIG. 6A illustrates a perspective view of a human strand of hair that had never been contacted with mascara.

FIG. 6A illustrates a strand of hair that had never been contacted with mascara. FIG. 6B illustrates the hair of FIG. 6A, to which a shakable mascara embodiment had been applied. Mascara clumping and uneven distribution were not observable.

Figure 7B:
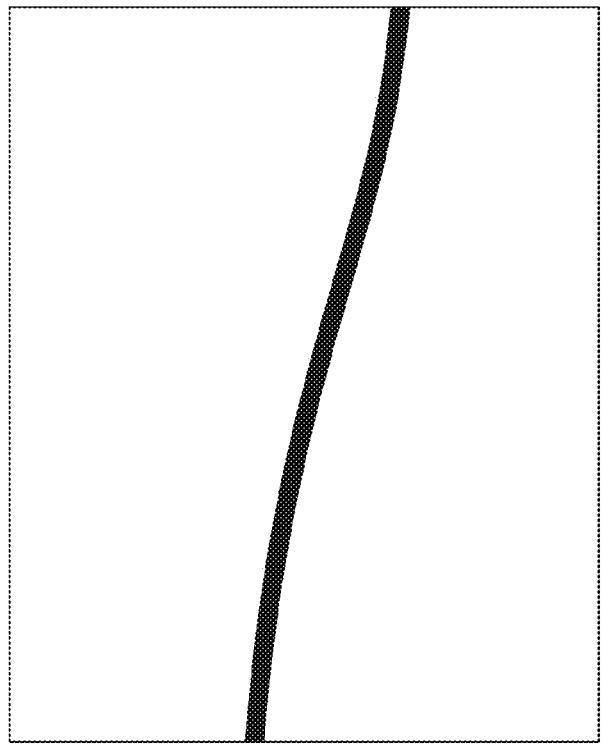
FIG. 7B illustrates a perspective view of the hair of FIG. 7A that had been contacted with a shakable mascara embodiment, for twelve weeks.
Figure 7A:
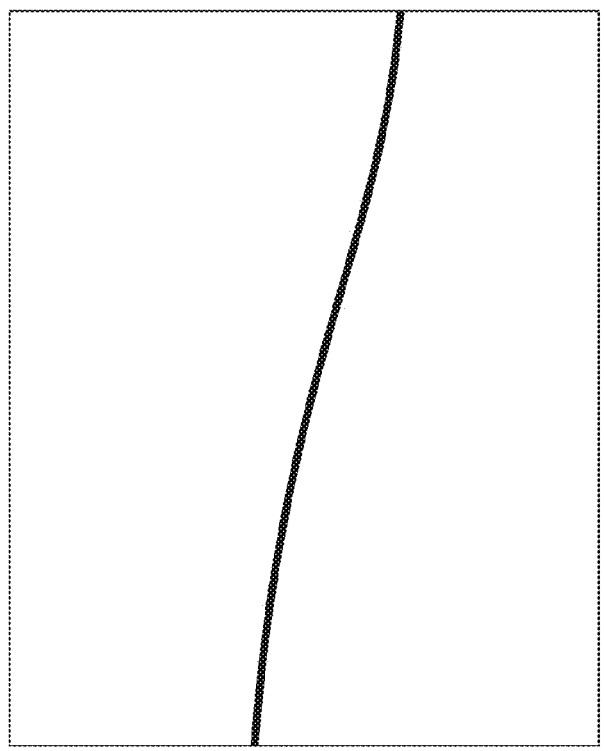
FIG. 7A illustrates a perspective view of a human strand of hair that had never been contacted with mascara.

FIG. 7A illustrates a strand of hair that had never been contacted with mascara. FIG. 7B illustrates the hair of FIG. 7A, to which a shakable mascara embodiment had been applied over a period of twelve weeks. Mascara clumping and uneven distribution were not observable.

It will be readily understood to those skilled in the art that various other changes in the details, material, and arrangements of the parts and method stages which have been described and illustrated in order to explain the nature of this inventive subject matter may be made without departing from the principles and scope of the inventive subject matter as expressed in the subjoined claims.

What is claimed is:

1. A shakeable gel mascara comprising:

| Ingredient | % w/w |
| --- | --- |
| Water | 61.5300 |
| Iron Oxides | 10.0000 |
| Beeswax | 5.6000 |
| Carnauba Wax | 4.8000 |
| Paraffin | 3.8400 |
| Nylon-6/12 | 2.000 |
| Disodium EDTA | 0.0900 |
| Candelilla Wax | 1.6000 |
| Polysorbate 20 | 2.4250 |
| Lithium Magnesium Sodium Silicate | 1.5000 |
| Ammonium Acrylates Copolymer | 0.7350 |
| Cyclopentasiloxane | 0.8000 |
| Hydrogenated Palm Glycerides | 1.2250 |
| Potassium Cetyl Phosphate | 1.2750 |
| Stearic Acid | 0.8000 |
| Phenoxyethanol | 0.8091 |
| Trimethylsiloxysilicate | 0.8000 |
| Sodium Hydroxide | 0.0800 |
| Ethylhexylglycerin | 0.0900 |
| Tocopherol | 0.0009. |

2. A method of making a shakeable gel volume mascara, comprising:
    preparing a first phase of deionized water and disodium ethylenediaminetetraacetic acid (EDTA) by adding the disodium EDTA to the deionized water;
    adding a surfactant to the first phase to make a second phase;
    preparing a colloidal dispersion;
    adding a particulate colorant to the colloidal dispersion to make a third phase and adding the third phase to the second phase to make a fourth phase; and
    preparing a wax phase comprising one or more of stearic acid, carnauba wax, paraffin wax, candelilla wax or beeswax to make a wax phase and adding the wax phase to the third phase to make a fifth phase; and
    adding phenoxyethanol and ethylhexylglycerin to the fifth phase to make the gel volume mascara.

3. The method of claim 2, further comprising adding a phase to the first phase of deionized water and disodium EDTA that comprises a synthetic layered silicate with low heavy metals content.

4. The method of claim 3, further comprising potassium cetyl phosphate and hydrogenated palm glycerides, added to the second phase.

5. A shakeable mascara, comprising:
    Hard and soft waxes;
    A film-forming complex comprising cyclopentasiloxane and trimethysiloxysilicate;
    Water;
    Lithium magnesium sodium silicate; and
    Iron oxide.

6. The shakeable mascara of claim 5, further comprising isopropyl alcohol and ammonium acrylates copolymer.

7. The shakeable: mascara of claim 5, further comprising hydrogenated palm glycerides.

8. The shakeable mascara of claim 5, further comprising potassium cetyl phosphate.

9. A shakeable mascara, comprising:
    Hard and soft waxes in a concentration of 5% to 16% by weight of the shakeable mascara; and
    A film-forming complex comprising cyclopentasiloxane and trimethysiloxysilicate.

10. The shakeable mascara of claim 9, further comprising a thixotropic gel.

11. The shakeable mascara of claim 9, further comprising water.

* * * * *